United States Patent [19]

Failli et al.

[11] 4,018,912
[45] Apr. 19, 1977

[54] TRIPEPTIDE DERIVATIVES WITH CENTRAL NERVOUS SYSTEM ACTIVITY AND PREPARATION THEREOF

[75] Inventors: Amedeo Failli, Montreal; Hans U. Immer, Mount Royal; Manfred Götz, Hudson, all of Canada

[73] Assignee: Ayerst McKenna and Harrison Ltd., Montreal, Canada

[22] Filed: July 28, 1975

[21] Appl. No.: 599,450

[52] U.S. Cl. .......................... 424/177; 260/112.5 R
[51] Int. Cl.² ................ A61K 37/00; C07C 103/52
[58] Field of Search ............. 260/112.5 R; 424/177

[56] References Cited
UNITED STATES PATENTS 3,888,840  6/1975  Failli et al. .................. 260/112.5 R

*Primary Examiner*—Lewis Gotts
*Assistant Examiner*—Reginald J. Suyat
*Attorney, Agent, or Firm*—Stephen Venetianer

[57] ABSTRACT

The tripeptide derivatives of formula 1

$$H-L-Pro-N(R^1)CH(R^2)CO-Y-R^3 \qquad (1)$$

in which $R^1$ is hydrogen, lower alkyl or $NR^4R^5$ wherein $R^4$ and $R^5$ each are lower alkyl, $R^2$ is hydrogen or lower alkyl, $R^3$ is amino, lower alkylamino, di(lower)alkylamino or amino(lower)alkylamino and Y is one of the amino acid residues Gly or D-Ala with the proviso that when $R^1$ is $NR^4R^5$ wherein $R^4$ and $R^5$ are as defined herein and $R^2$ and Y are as defined herein, $R^3$ is lower alkylamino, di(lower)alkylamino or amino(lower)alkylamino, and a method for their preparation are disclosed. The tripeptide derivatives of formula 1 possess central nervous system activity and methods for their use are given.

21 Claims, No Drawings

TRIPEPTIDE DERIVATIVES WITH CENTRAL NERVOUS SYSTEM ACTIVITY AND PREPARATION THEREOF

BACKGROUND OF THE INVENTION a. Field of Invention

The present invention relates to tripeptide derivatives with central nervous system activity, to a process for their preparation, and to intermediates therefor.

b. Description of the Prior Art

The main obstacle to the practical use of many biologically active peptides is their brief period of action which is partly due to their inactivation by proteolytic enzymes. An example of such a peptide is the tripeptide which is the factor inhibiting release of the melanocyte stimulating hormone (MIF or MRIH).

This tripeptide was isolated from bovine hypothalamic tissue by R.M.G. Nair et al., Biochem. Biophys. Res. Commun., 43, 1376 (1971) and its structure was established as the C-terminal tripeptide of oxytocin: H-L-prolyl-L-leucyl-glycinamide.

This tripeptide was shown to exert an action on the central nervous system (CNS). The tripeptide potentiates the behavioral effects of (3,4-dihydroxyphenyl)-L-alanine (L-DOPA) as shown by N. P. Plotnikoff et al., Life Sciences, 10, part 1, 1279 (1971) and E. Friedman et al., Science, 182, 831 (1973). The tripeptide antagonizes the effects of oxotremorine [N. P. Plotnikoff et al., Proc. Soc. Exp. Biol. Med., 140, 811 (1972)] and reverses the sedative effects of deserpidine in mice and monkeys [N. P. Plotnikoff et al., Neuroendocrinology, 11, 67 (1973)]. On the basis of the above biological activities A. V. Schally et al., Science 179, 341 (1973) have suggested that the tripeptide H—Pro—Leu—Gly—$NH_2$ could be useful in the treatment of patients suffering from depression or parkinsonism.

Since the elucidation of the structure of the above tripeptide, a limited number of analogs of this peptide have been synthesized by M. E. Celis et al., Febs Letters, 27, 327 (1972) and S. Castensson et al., Febs Letters, 44, 101 (1974). However, the natural tripeptide and the analogs known to date have the disadvantage of possessing a short duration of action due to rapid inactivation in the mammalian body and T. W. Redding et al., Neuroendocrinology, 11, 92 (1973) have demonstrated that the first step in the inactivation of the natural tripeptide appears to be proteolytic cleavage of the Pro-Leu bond with formation of proline and leucyl-glycinamide.

Accordingly, analogs of the natural tripeptide having a greater resistance to protease hydrolysis while retaining the CNS activity of the natural tripeptide are of interest. The present invention discloses novel analogs of the natural tripeptide in which the leucyl and glycyl amino acid residues may be replaced and the peptide linkage and the terminal amide may be substituted.

In addition, an unique and straightforward process for preparing these tripeptide derivatives is disclosed.

SUMMARY OF THE INVENTION

The peptide derivatives of this invention are represented by the general formula 1.

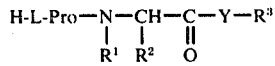

in which $R^1$ is hydrogen, lower alkyl or $NR^4R^5$ wherein $R^4$ and $R^5$ each are lower alkyl; $R^2$ is hydrogen or lower alkyl; $R^3$ is amino, lower alkylamino, di(lower)alkylamino or amino(lower)alkylamino and Y is one of the amino acid residues Gly or D—Ala with the proviso that when $R^1$ is $NR^4R^5$ wherein $R^4$ and $R^5$ are as defined herein and $R^2$ and Y are as defined herein, $R^3$ is lower alkylamino, di(lower)alkylamino or amino(lower)alkylamino.

One embodiment of the process of this invention proceeds through a series of intermediates of the formula (2)

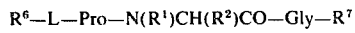

in which $R^1$ is lower alkyl or $NR^4R^5$ in which $R^4$ and $R^5$ are each lower alkyl, $R^2$ is hydrogen or lower alkyl, $R^6$ is an amino protective group as used in peptide synthesis, and $R^7$ is hydroxyl, lower alkoxy, amino, lower alkylamino, di(lower)alkylamino, amino(lower)alkylamino, or protected amino(lower)alkylamino.

The process comprises the condensation of an enamine or hydrazone of formula 3, $R^1N = CHR^2$, in which $R^1$ and $R^2$ are as defined immediately above with an amino acid of the formula $R^6$—L—Pro—OH in which $R^6$ is as defined immediately above in the presence of an isonitrile of the formula $CNCH_2COR^7$ in which $R^7$ is lower alkoxy, to obtain the corresponding intermediate of formula 2 in which $R^1$, $R^2$, and $R^6$ are as defined immediately above and $R^7$ is lower alkoxy. Transformation of said last-named compound by standard procedures known to be effective for transforming lower alkyl ester into the corresponding amide or substituted amide gives the corresponding compound of formula 2 in which $R^7$ is amino, lower alkylamino, di(lower)alkylamino, or protected amino(lower)alkylamino, and removed of the protective group(s) gives the corresponding compound of formula 1.

The preferred process used in the above embodiment comprises the condensation of a compound of formula 3 with an amino protected proline of formula $R^6$—L—Pro—OH in which $R^6$ is as defined herein, in the presence of an isonitrile of formula $CNCH_2COR^7$ in which $R^7$ is as defined herein to obtain the corresponding intermediate of formula 2 in which $R^1$, $R^2$, $R^6$ and $R^7$ are as defined immediately above, followed by treatment of said intermediate 2 with ammonia to obtain the corresponding amide; and removing the protective group $R^6$ to obtain the corresponding peptide derivative of formula 1 in which $R^1$ and $R^2$ are as defined immediately above, $R^3$ is amino and Y is the amino acid residue Gly.

Alternatively, the intermediate of formula 2 in which $R^1$, $R^2$, $R^6$ and $R^7$ are as defined immediately above is treated with a hydrolyzing agent to obtain the corresponding acid of formula 2 in which $R^1$, $R^2$ and $R^6$ are as defined immediately above and $R^7$ is hydroxyl. The latter acid is treated with an agent generally useful in peptide chemistry for activating a carboxyl group, and condensing the activated compound with a lower alkylamine, di(lower)alkylamine or mono protected amino(lower)alkylamine gives the corresponding intermediate of formula 2 in which $R^1$, $R^2$ and $R^6$ are as defined immediately above and $R^7$ is lower alkylamino, di(lower)alkylamino or protected amino(lower)alkylamino. The protective group(s) in said last-named compound are removed to obtain the corresponding tripeptide derivative of formula 1 in which $R^1$ and $R^2$ are as defined immediately above, $R^3$ is alkylamino, di(lower)alkylamino, or amino(lower)alkylamino, and Y is the amino acid residue Gly.

A further alternate embodiment of the process of this invention comprises the preparation of tripeptide derivatives of formula 1 by the stepwise addition of amino acids. Preferred compounds of formula 1 obtained by this alternate embodiment are those in which $R^1$ is hydrogen or lower alkyl, $R^2$ is hydrogen or lower alkyl, preferably an amino acid side chain, $R^3$ is amino, lower alkylamino, di(lower)alkylamino or amino(lower)alkylamino and Y is the amino acid residue Gly or D—Ala.

The tripeptide derivative of formula 1 in which $R^1$ is $CH_3$, $R^2$ is $CH_2CH(CH_3)_2$, i.e. the amino acid side chain of L-leucine, $R^3$ is $NH_2$ and Y is the amino acid residue D—Ala is readily prepared by coupling an activated ester of benzyloxycarbonyl-L-(N-methyl)leucine with D-alanice methyl ester to obtain the dipeptide of formula Z—L—(N—Me)Leu—D—Ala—OMe. The amino protecting group (Z) of the latter compound is removed, followed by coupling with an activated ester of benzyloxycarbonyl-L-proline to give the tripeptide of formula Z—L—Pro—L—(N—Me)-Leu—D—Ala—OMe. The latter compound, when subjected to the action of ammonia in an inert organic solvent, gives the tripeptide of formula Z—L—Pro—L—(N—Me)Leu—D—Ala—$NH_2$. The amino protecting group (Z) of the latter compound is removed to obtain the corresponding tripeptide derivative of formula 1 in which $R^1$ is $CH_3$, viz., H—L—Pro—L—(N—Me)Leu—D—Ala—$NH_2$.

The tripeptide of formula 1 in which $R^1$ is hydrogen, $R^2$ is $CH_2CH(CH_3)_2$, $R^3$ is $NH(CH_2)_4NH_2$ and Y is the amino acid residue Gly is readily prepared by subjecting the tripeptide of formula Z—L—Pro—L—Leu—Gly—OEt to hydrolysis to obtain the corresponding acid of formula Z—L—Pro—L—Leu—Gly—OH. The carboxyl of said last-named compound is activated and condensed with a mono protected amino-1,4-diaminobutane, for example $H_2N(CH_2)_4NHBoc$ to give the corresponding tripeptide of formula Z—L—Pro—L—Leu—Gly—$NH(CH_2)_4NH$—Boc. The amino protecting groups of the latter compound are removed to obtain the corresponding tripeptide derivative of formula 1, viz., L—Pro—L—Leu—Gly—$NH(CH_2)_4NH_2$.

DETAILS OF THE INVENTION

The term "lower alkyl" as used herein contemplates straight chain alkyl radicals containing from one to six carbon atoms and branched chain alkyl radicals containing three to four carbon atoms excluding t-butyl and includes methyl(Me), ethyl (Et), propyl, isopropyl, butyl, isobutyl, pentyl and the like.

In general the abbreviations used herein for designating the amino acids and the protective groups are based on recommendations of the IUPAC-IUB Commission on Biochemical Nomenclature see Biochemistry, 11, 1726–1732 (1972). For instance Pro, Leu, Ala and Gly represent "residues" of proline, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —$CH(NH_2)COOH$ portion, as defined by K. D. Kopple, "Peptides and Amino Acids", W. A. Benjamin Inc., New York and Amsterdam, 1966, pages 2 and 33; examples of such side chains of the common amino acids are —$CH_2CH(CH_3)_2$ (the side chain of leucine) or H— (the side chain of glycine).

The configuration of the amino acids and amino acid residues herein are designated by the appropriate symbols D, L or DL, furthermore when the configuration is not designated the amino acid or residue can have the configuration D, L or DL. It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis and have arbitrarily been named as isomers A or B, respectively.

A number of procedures or techniques for the preparation of peptides have hitherto been well established and found in general textbooks of peptide chemistry; for example K. D. Kopple, supra, pp. 33–51 and E. Schröder and K. L. Lübke, "The Peptides"; Vol. 1; Academic Press, New York, 1965, pp. 3–128. For instance, the functional groups which are not involved in the peptide bond formation reaction are optionally protected by a protecting group or groups prior to the condensation reaction. Examples of protecting groups for an amino function of a peptide or amino acid not involved in the peptide bond formation are: the alkoxycarbonyls which include benzyloxycarbonyl (represented by Z), t-butoxycarbonyl (Boc), or α,α-dimethyl-3,4-dimethoxybenzyloxycarbonyl (Ddz); the acyl type protecting groups which include triphenylmethyl or benzyl. The preferred protecting groups are benzyloxycarbonyl and t-butoxycarbonyl. The carboxylic acid function of a peptide or amino acid can be considered protected by a lower alkyl or lower aralkyl ester which includes methyl (represented by OMe), ethyl (OEt), benzyl (OBzl) or tert-butyl (OBu$^t$).

To promote facile condensation of a peptide carboxyl group with a free amino group of another peptide to form a new peptide bond, the terminal carboxyl group must be activated. Descriptions of such carboxyl-activating groups are included in the general textbooks of peptide chemistry by Kopple, or Schröder and Lübke, cited above. Examples of the activated form of a terminal carboxyl are acid chloride, anhydride, azide, imidazolide, activated ester or O-acyl urea of a dialkylcarboxdiimide. The following activated esters have proved to be particularly suitable in the process of this invention: 2,4,5-trichlorophenyl (represented by OTcp), pentachlorophenyl (OPcp), p-nitrophenyl (ONp), or L-benzotriazolyl; the succinimido derivative is also useful for this purpose.

The terms "peptide, dipeptide, tripeptide, and the like" used herein are not limited to refer to the respective parent peptides but also are used in reference to modified peptides having functionalized or protecting groups. The term "peptide" as used herein is used in reference to a peptide with one to three amino acid residues.

The term "mineral acid" as used herein contemplates the strong inorganic acids and includes hydrochloric, hydrobromic, sulfuric, and phosphoric acid. When the term is used in conjunction with an anhydrous system, anhydrous hydrochloric acid is the preferred mineral acid.

The term "mildly acidic conditions" as used herein contemplates conditions in which a dilute aqueous solution of an organic acid, for example 30–90%, preferably 70–80%, aqueous formic, acetic or propionic acid, or 1 to 10% aqueous trifluoroacetic acid is a principal component of the reaction medium, usually at 20°–50° C.

The term "moderately acidic conditions" as used herein contemplates conditions in which concentrated organic acids or aqueous solutions of the mineral acids are used as a principal component of the reaction medium at termperatures ranging from about −30° to 30° C. Examples of preferred conditions in this case include the use of 50 to 100% trifluoroacetic acid at 0° to 30° C, 0.1 to 12N hydrochloric acid at −30° to 10° C or 0.1 to 6N hydrogen chloride in an anhydrous inert organic solvent.

The term "organic base" as used herein includes triethylamine, N-ethylmorpholine and N-ethyldiisopropylamine.

The term "strong base" as used herein contemplates both organic bases, as described above, and strong inorganic bases including the hydroxides and carbonates of sodium and potassium.

The tripeptides of this inventin are obtained in the form of the free base or as an acid addition salt directly from the process of this invention. The tripeptides in the form of the free base are readily obtained from the corresponding acid addition salt by conventional methods, for example the free base is readily obtained from the acetic acid addition salt by repeated lyophilization of the latter salt from aqueous solution. The acetic acid addition salt is readily obtained from another acid addition salt by treatment with the appropriate ion exchange resin in the manner hereinafter disclosed. The tripeptides of this invention are obtained in the form of a pharmaceutically acceptable acid addition salt either directly from the process of this invention or by reacting the tripeptide with one or more equivalents of the appropriate acid. Examples of preferred non toxic salts are those with pharmaceutically acceptable organic acids, e.g. acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g. hydrochloric acid, or sulfuric acid, or phosphoric acid. It should be noted that the tripeptides of this invention have one or two basic nitrogens giving rise to addition salts with one to possibly two equivalents of acid. If desired a particular acid addition salt is converted into another acid addition salt, e.g., a salt with a non toxic, pharmaceutically acceptable acid, by treatment with the appropriate ion exchange resin in the manner described by R. A. Boissonas, et al., Helv. Chim. Acta, 43, 1349 (1960). Suitable ion exchange resins are cellulose based cation exchangers, for example carboxymethylcellulose, or chemically modified, cross-linked dextran cation exchangers, for example, those of the Sephadex C type, and strongly basic anion exchange resins, for example those listed in J. P. Greestein and M. Winitz "Chemistry of the Amino Acids", John Wiley and Sons, Inc., New York and London, 1961, Vol. 3, p. 1456.

The tripeptide derivatives produced by the process of this invention, as well as their corresponding pharmaceutically acceptable salts, are useful because they show the pharmacological activities upon the CNS of warm-blooded animals possessed by the natural tripeptide H-L-prolyl-L-leucyl-glycinamide, and at least one of the compounds of this invention shows activities greater than those of the natural tripeptide. For example, the compounds of this invention potentiate the effects of L-DOPA when tested by the method G. M. Everett, Proc. First Internat. Symps. Antidepr. Drugs, Excerpta Medica Internat. Congr. Series no. 122, 164 (1966) in the modification described by N. P. Olotnikoff et al., Life Sciences Vol. 10, Part 1, p. 1279 (1971). The tripeptide derivatives of formula 1 also antagonize fluphenazine-induced catalepsy in rats, an animal model particularly suitable for screening compounds useful in the management of Parkinson-like diorders, and they cause reversal of the sedative effect of deserpidine. The tripeptide derivatives of this invention have a prolonged duration of action and are useful for treating or managing central nervous system disorders, especially Parkinsonism or mental depression, in warm-blooded animals. When a tripeptide of this invention or a slat is employed for such treatment or management, it is administered systemically, preferably parenterally, in combination with a pharmaceutically acceptable liquid or solid carrier. The peptides of formula 1 have a lower order of toxicity. The proportion of the tripeptide or salt thereof is determined by its solubility in the given carrier, by the given carrier, by the chosen route of administration and by standard biological practice. For parenteral administration to animals the tripeptide or a salt thereof is used in a sterile aqueous solution which may also contain other solutes such as buffers or preservatives, as well as sufficient pharmaceutically acceptable salts or glucose to make the solution isotonic. The dosage will vary with the form of administration and with the particular species of animal to be treated and is preferably kept at a level of from 0.05 mg to 20 mg per kilogram body weight. However, a dosage level in the range of from about 0.05 mg to about 2 mg per kilogram body weight is most desirably employed in order to achieve effective results.

For oral administration to animals the dosage of the tripeptide or a salt thereof is preferably kept at a level of from 0.25 mg to 100 mg per kilogram body weight, and the compound is formulated in unit dosage form with pharmaceutically acceptable carriers. The tripeptide or a salt thereof may also be administered directly to the interior surface of the mouth, for example in one of the dosage forms described in U.S. pat. application Ser. No. 567,788, filed Apr. 14, 1975.

The tripeptide or a salt thereof may also be administered in one of the long acting, slow-release or depot dosage forms described below, preferably by intramuscular injection or by implantation. Such dosage forms are designed to release from about 0.05 mg to about 2 mg per kilogram body weight per day.

It is often desirable to administer a tripeptide of formula 1 continuously over prolonged periods of time in long-acting, slow-release, or depot dosage forms. Such dosage forms may either contain a pharmaceutically acceptable salt of the tripeptide having a low degree of solubility in body fluids, for example one of those salts described below, or they may contain the tripeptide in the form of a water-soluble salt together with a protective carrier which prevents rapid release. In the latter case, for example, the tripeptide may be formulated with a nonantigenic partially hydrolyzed gelatin in the form of a viscous liquid; or the tripeptide may be absorbed on a pharmaceutically acceptable solid carrier, for example, zinc hydroxide, and may be administered in suspension in a pharmaceutically acceptable liquid vehicle; or the tripeptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton; Pa, 1970. Long-acting, slow-release preparations of the tripeptide produced according to the process of this inention may also be obtained by microencapsulation in a pharmaceutically acceptable coating, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York 1967, pp. 436–456. Such formulations, as well as suspensions of salts of the tripeptide which are only sparingly soluble in body fluids, for example the salt with pamoic acid, are designed to release from about 0.05 mg to about 2 mg of the active compound per kilogram body weight per day, and are preferably administered by intramuscular injection. Alternatively, some of the solid dosage forms listed above, for example certain sparingly water-soluble salts or dispersions in or adsorbates on solid carriers of slats of the agent, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

Process

The process of this invention is illustrated by the following description of preferred embodiments.

In the practice of an embodiment of the process of this invention the first group of requisite starting materials, the enamines or hydrazones of formula 3, $R^1N = CHR^2$ in which R is lower alkyl or $NR^4R^5$ in which $R^4$ and $R^5$ are lower alkyl and $R^2$ is hydrogen or lower alkyl are prepared by condensing an appropriately substituted amine of formula $R^1NH_2$ or a hydrazine of formula $R^4R^5NNH_2$ in which $R^1$, $R^4$ $R^5$ are as defined immediately above, with an aldehyde of formula $R^2CHO$ in which $R^2$ is as defined above.

The amines of formula $R^1NH_2$ or the hydrazines of formula $R^4R^5NNH_2$ are either known or they are prepared by known methods. Likewise, the aldehydes of formula $R^2CHO$ are known and most are commercially available.

The condensation of the amine of formula $R^1NH_2$ or of the hydrazine of formula $R^4R^5NNH_2$ with the aldehyde of formula $R^2CHO$ is preferably carried out in an inert solvent at an elevated temperature, at or near the reflux temperature of the mixture. Either an anhydrous, water-immiscible hydrocarbon solvent, for example, benzene or toluene, with concomitant physical removal of water as it is being formed, for example, by means of a Dean-Stark water separator, or a lower alkanol solvent, for example, ethanol, propanol, or isopropanol may be employed. Thereafter, evaporation of the solvent and purification of the residue, for example by distillation or crystallization, yields the corresponding enamine or hydrazone of formula 3. Alternatively, the desired enamine or hydrazone may be prepared in situ during the course of the key reaction, see below.

The second group of requisite starting materials, the amino protected acids of formula $R^6$—L—Pro—OH in which $R^6$ is as defined hereinbefore are known. For example, t-butoxycarbonyl-L-proline (Boc—L—Pro—OH) and benzyloxycarbonyl-L-proline (Z—L—Pro—OH) are described by G. R. Anderson and A. C. McGregor, J. Amer. Chem. Soc., 79, 6180 (1957) and W. Grassmann and E. Wünsch, Chem. Ber., 91, 462 (1958), respectively.

The third group of requisite starting materials, the isonitriles of formula $CNCH_2COR^7$ in which $R^7$ is lower alkoxy with 1–3 carbon atoms are either known, e.g. ethyl isocyanoacetate is described by R. Appel et al., Angew. Chem., Int. ed., 10, 132 (1972) or are easily prepared by known methods.

Next, in a key reaction of the process of this invention the aforementioned enamine or hydrazone of formula 3, or alternatively the desired anamine or hydrazone prepared in situ from the respective amine or hydrazine and aldehyde, is condensed with the acid of formula $R^6$—L—Pro—OH and the isonitrile of formula $CNCH_2COR^7$ to yield the corresponding intermediate of the formula $R^6$—L—Pro—N($R^1$)—CH($R^2$)CO—Gly—$R^7$ (2) in which $R^1$, $R^2$, $R^6$ and $R^7$ are as defined immediately above.

Although not critical, it is preferable to use approximately equimolar amounts of the requisite starting materials for this condensation. The condensation is effected most conveniently in an inert solvent, for example, in halogenated hydrocarbons including methylene chloride, chloroform, and carbon tetrachloride; in ethers and cyclic ethers including dioxane, diethyl ether and tetrahydrofuran; or in lower aliphatic alcohols including methanol, ethanol and propanol. However, when the starting materials are mutually soluble or the mixture thereof becomes liquid during the course of the condensation the solvent may be omitted without any deleterious effects.

The temperature and duration of the condensation are also not critical. The reaction may be performed at temperatures ranging from −20° to 100° C; however, a range from 10° to 40° C is most convenient. The reaction time may be varied and depends on the reactivity of the various starting materials; however, reaction times from 15 minutes to several days are employed generally, with six hours to two days being preferred.

Thereafter, the intermediate of formula 2 in which $R^1$, $R^2$, $R^6$ and $R^7$ are as defined immediately above is isolated and purified according to standard procedures. For instance the product is extracted with a water-immisicible solvent and, if needed, purified by chromatography and crystallization.

It will be apparent to those skilled in the art that the amino acid residue represented in formula 2 by —N($R^1$)CH($R^2$)CO—to as obtained in this reaction must be racemic, and it is therefore designated in this Application by the prefix DL, except when $R^2$ is hydrogen and the above amino acid residue represents the amino acid residue of glycine. Also, it is apparent that the intermediate of formula 2 exists in the form of two geometric isomers which may be separated, for example by chromatography on silica gel. For convenience, these two isomers are designated arbitrarily as isomers A and B. Thereafter either the separate isomers or the mixtures thereof are transformed to the corresponding peptide derivatives of formula 1 in the manner disclosed below.

Said intermediate of formula 2 is subjected to amidation, to obtain the intermediate amide of formula 2 in which $R^1$, $R^2$, $R^6$ are as defined immediately above and $R^7$ is $NH_2$. Preferred conditions for this amidation include treating said intermediate with a substantially saturated solution of ammonia in an inert solvent, for example, methanol, ethanol or tetrahydrofuran, at 0° to 20° C for 6 hours to 4 days. If desired the corresponding amide thus obtained may be separated into two isomers at this stage. This separation is effected conveniently by chromatography on silica gel.

The above amide is then treated with a deprotecting agent to obtain the corresponding tripeptide derivative of formula 1 in which $R^1$ is lower alkyl or $NR^4R^5$ wherein $R^4$ and $R^5$ each are lower alkyl, $R^2$ is hydrogen or lower alkyl, $R^3$ is amino and Y is the amino acid residue Gly. The tripeptide derivative of formula 1 in which $R^1$ is $NR^4R^5$ wherein $R^4$ and $R^5$ each are lower alkyl, $R^2$ is hydrogen or lower alkyl, $R^3$ is amino and Y is the amino acid residue Gly has been disclosed in the copending U.S. patent application Ser. No. 330,352, filed Feb. 7, 1973.

The above deprotecting reaction when $R^6$ is benzyloxycarbonyl (Z) is achieved conveniently by subjecting said amide to hydrogenation in the presence of a noble metal catalyst. Preferred noble metal catalysts for effecting the above and other hydrogenations in the process of this invention include those of palladium and platinum, for example, 5% palladium on charcoal or 5% platinum on charcoal; the hydrogenation itself being performed in an inert solvent, for example, acetic acid, methanol, ethyl acetate and the like. In the present instance the hydrogenation is preferably carried out with 5% palladium on charcoal in methanol whereby the hydrogenation product, the corresponding tripeptide derivative of formula 1, is obtained in the form of the free base by separating the catalyst from the reaction mixture and evaporating the solvent. The deprotecting reaction when $R^6$ is t-butoxycarbonyl is achieved conveniently by subjecting said amide to moderately acidic conditions to obtain the corresponding deprotected compound. In practising the above deprotecting reaction it is convenient to dissolve said amide in an excess of trifluoracetic acid or in an inert organic solvent, for example, ethyl acetate or tetrahydrofuran substantially saturated with anhydrous hydrogen chloride. After completion of the reaction, evaporation gives directly the aforementioned deprotected tripeptide derivative of formula 1 in the form of the acid addition salt of the corresponding acid. The latter acid addition salt may be converted to its corresponding tripeptide derivative of formula 1 in the form of the free base by standard means.

The tripeptide derivative of formula 1, in which $R^1$ is $NR^4R^5$ wherein $R^4$ and $R^5$ each are lower alkyl; $R^2$ is $CH_2CH(CH_3)_2$; $R^3$ is $NH(CH_2)_4NH_2$ and Y is the amino acid residue Gly, is prepared by treating the intermediate of formula 2 in which $R^1$ is $NR^4R^5$ wherein $R^4$ and $R^5$ each are lower alkyl and $R^2$ is $CH_2CH(CH_3)_2$, $R^6$ is an amino protecting group and $R^7$ is lower alkoxy with a hydrolyzing agent to obtain the corresponding acid of the intermediate of formula 2 in which $R^1$, $R^2$ and $R^6$ are as defined herein and $R^7$ is hydroxyl. For basic hydrolysis a preferred method involves subjecting the lower alkyl ester to the action of a strong base, for example, sodium or potassium hydroxide, in the presence of sufficient water to effect hydrolysis of the ester. The hydrolysis is performed using a suitable solvent, for example, methanol or ethanol. The reaction mixture is maintained at a temperature of from 0° to 50° C, preferably 20° to 30° C, until hydrolysis occurs. Usually from 10 to 30 hours is sufficient for this hydrolysis. The reaction mixture is then rendered acidic with an acid, for example, hydrochloric acid, sulfuric acid and the like, and extracted with a substantially water immiscible organic solvent, preferably chloroform. The organic solvent is evaporated to obtain said corresponding acid.

The above corresponding acid is treated with a reagent for transforming an amino or peptide acid to a corresponding compound having an activated carboxyl and condensed with mono(t-butoxycarbonyl)-1,4-diaminobutane. A preferred method in practising this reaction is effected by reacting the corresponding acid with an approximately equimolar amount of $N,N^1$-carbonyldiimidazole in an inert organic solvent, preferably dimethylformamide, at about −20° to −10° C for about 20 to 50 minutes. The compound having an activated carboxyl is treated with a solution of a substantially equimolar amount of mono mono(t-butoxycarbonyl)-1,4-diaminobutane hydrochloride, described by R. Geiger, Annalen, 750, 165 (1971), and an organic base, preferably triethylamine, in an inert organic solvent, preferably dimethylformamide. The mixture is stirred at about 20° to 30° C for about 15 to 30 hours and evaporated. The residue is taken up in a substantially water immiscible solvent, preferably ethyl acetate, washed and evaporated. The residue is subjected to chromatography on silica gel using mixtures of halogenated hydrocarbon, lower alkanols, and organic bases, preferably chloroform-methanol-pyridine for elution to obtain the two Isomers A and B of the amino protected intermediate of formula 2 Z—L—Pro—N($NR^{4R5}$)CH[$CH_2$CH—($CH_3$)$_2$]CO—Gly—NH($CH_2$)$_4$—NH—Boc in which $R^4$ and $R^5$ are as defined herein.

Thereafter the protective groups Z and Boc are removed from said last-named compound to obtain the tripeptide derivative of H—L—Pro—N($NR^4R^5$)CH[$CH_2$CH($CH_3$)$_2$]CO—Gly—NH($CH_2$)$_4$$NH_2$, i.e. the compound of formula 1 in which $R^1$ is $NR^4R^5$ wherein $R^4$ and $R^5$ each are lower alkyl, $R^2$ is $CH_2CH(CH_3)_2$, $R^3$ is $NH(CH_2)_4NH_2$ and Y is the amino acid residue Gly.

The two amino protective groups Z and Boc may be removed simultaneously, for example, by using a strong acid, i.e. hydrobromic acid in acetic acid or hydrofluoric acid, or preferably the deprotection is achieved in a stepwise manner. The amino protected intermediate described above is subjected to hydrogenation as shown above in the presence of a noble metal catalyst in an inert solvent, preferably 5% palladium on charcoal in acetic acid, in order to remove the amino protecting group, benzyloxycarbonyl(Z). The mixture is filtered and cooled to about 0° to 10° C and treated with a moderately strong acid to remove the remaining amino protecting group, t-butoxycarbonyl(Boc). An example of such an acid is hydrogen chloride. The anhydrous acid is either added directly to the above filtrate or a solution of the acid in an inert organic solvent, for example, ethyl acetate, tetrahydrofuran and the like, is added. The mixture is stirred at about 0° to 25° C for about one to three hours and evaporated. The residue is subjected to chromatography on a column of a cross-linked dextran absorbent (Sephadex LH-20) using methanol as eluant to obtain said last-named tripeptide derivative of formula 1 as the hydrochloric acid addition salt. The free base of the said last-named tripeptide derivative of formula 1 is obtained by conventional methods, for example by conversion to the acetate salt followed by lyophilization.

An alternative embodiment of the process of this invention is the preparation of tripeptide derivatives of formula 1 by the stepwise addition of amino acids.

The intermediate described above, Boc—L—Pro—L—(N—Me)Leu—Gly—OEt, i.e. the compound of formula 2 in which $R^1$ is $CH_3$, $R^2$ is $CH_2CH(CH_3)_2$ and $R^7$ is OEt is also prepared readily by the stepwise addition of amino acids.

In a preferred embodiment of this alternative preparation of said last-named intermediate of formula 2, the starting material benzyloxycarbonyl—L—(N-methyl)leucine, described by J. R. Coggins and N. L. Benoiton, Can. J. Chem., 49, 1968 (1971), is converted to its activated 2,4,5-trichlorophenyl ester by treating said starting material with substantially one molar equivalent of 2,4,5-trichlorophenol in an inert organic solvent, preferably methylene chloride or tetrahydrofuran, in the presence of 1.1 to 1.5 molar equivalents of dicyclohexylcarbodiimide at −20° to 0°to C for about 45 to 75 minutes and then at 20° to 30° C for one to three hours. The activated ester, i.e. the 2,4,5-trichlorophenyl ester of Z—L—(N—Me)Leu—OH, is then coupled with a substantially equimolar amount of glycine ethyl ester hydrochloride in the presence of an organic base, preferably N-ethylmorpholine, in an inert organic solvent, preferably dimethylformamide at 0° to 30° C for 10 to 24 hours to obtain the dipeptide of formula Z—L—(N—Me)Leu—Gly—OEt. Thereafter the amino protecting group, Z of said last-named compound is removed, preferably by dissolving the compound in acetic acid containing about three molar equivalents of hydrobromic acid and stirring at 20° to 30° C for four to five hours to obtain the dipeptide of formula H—L(N—Me)Leu—Gly—OEt as the hydrobromic acid addition salt. Said last-named dipeptide is coupled with the 1-benzotriazolyl ester of Boc—L—Pro—OH, which is prepared by combining Boc—Pro—OH with one to two molar equivalents of 1-hydroxybenzotriazole and 1.1. to 1.5 molar equivalents of dicylohexylcarbodiimide in an inert organic solvent, preferably tetrahydrofuran, at about −5° to 0° C. The mixture is stirred at about −5° to 0° C for about 1 hour and then at 20°to 30° C for an additional hour. This solution containing the 1-benzotriazolyl ester of Boc—L—Pro—OH is then combined at about −5° to 5° C with a solution containing a substantially equimolar amount of the above dipeptide H—L—(N—Me)-Leu—Gly—OEt in the form of its hydrobromic acid addition salt and an organic base, preferably N-ethylmorpholine in an inert organic solvent, preferably tetrahydrofuran. The mixture is stirred for about 30 minutes at about −5° to 5° C and then about about 20° to 30° C for about 30 to 50 hours to give Boc—L—Pro—L—(N—Me)Leu—Gly—OEt, i.e. the intermediate of formula 2, wherein $R^1$ is $CH_3$, $R^2$ is $CH_2CH(CH_3)_2$, and $R^7$ is OEt. Said last-named intermediate of formula 2 is identical in all respects to the isomer B of the intermediate of formula 2 obtained as described above.

The tripeptide derivative of formula 1 in which $R^1$ is $CH_3$, $R^2$ is $CH_2CH(CH_3)_2$, $R^3$ is $NH_2$ and Y is the amino acid residue D—Ala is readily prepared by condensing an activated ester of benzyloxycarbonyl-L-(N-methyl)-leucine, preferably the 1-benzotriazolyl ester, with D-alanine methyl ester to obtain the dipeptide of formula Z—L—(N—Me)Leu—D—Ala—OMe. The amino protecting group (Z) of the latter compound is removed followed by condensation with an activated ester of benzyloxycarbonyl-L-proline, preferably the p-nitrophenyl ester, to give the tripeptide of formula Z—L—Pro—L—(N—Me)Leu—D—Ala—OMe. The latter compound is subjected to the action of ammonia in an inert organic solvent to give the tripeptide amide of formula Z—L—Pro—L—(N—Me)-Leu—D—Ala—NH_2. The amino protecting group (Z) of the latter compound is removed to obtain the corresponding tripeptide derivative of formula 1 Z—L—Pro—L—(N—Me)Leu—D—Ala—NH_2.

In a preferred embodiment of the preparation of the latter tripeptide derivative of formula 1, substantially equimolar amounts of Z—L—(N—Me)Leu—OH, described by J. R. Coggins, supra, and H—D—Ala—OMe in an inert organic solvent, preferably dimethylformamide, are combined at about 0° to 10° C with 0.2 to 1.0 molar equivalents of 1-hydroxybenzotriazole and a substantially equimolar amount of an organic base, preferably N-ethylmorpholine. A solution of substantially equimolar amounts of dicyclohexylcarbodiimide in an inert organic solvent, preferably tetrahydrofuran is slowly added. After completion of addition the mixture is stirred at about 0° to 10° C for about one hour and at 20° to 30° C for another hour. After conventional purification the dipeptide of formula Z—L—(-N—Me)Leu—D—Ala—OMe is obtained.

Thereafter the amino protecting group (Z) of the latter dipeptide is removed, preferably by hydrogenation in the presence of a noble metal catalyst, preferably 5% palladium on charcoal, in an inert solvent, preferably acetic acid containing a substantially equimolar amount of a mineral acid, preferably hydrochloric acid. Removal of the catalyst and evaporation of the solvent gives the dipeptide of formula H—L—(-N—Me)Leu—D—Ala—OMe in the form of its hydrochloric acid addition salt. The latter compound is condensed with an activated ester of Z—L—Pro—OH. A practical and convenient method for this condensation comprises containing substantially equimolar amounts of the latter dipeptide acid addition salt, 1-hydroxybenzotriazole, benzyloxycarbonyl-L-proline p-nitrophenyl ester and N-ethylmorpholine in an inert organic solvent, preferably dimethylformamide at a temperature of about 0° to 10° C. The mixture is stirred at 0° to 10° C for about 2 to 4 days. After evaporation of the solvent the residue is dissolved in a substantially water immiscible organic solvent, preferably ethyl acetate, washed, dried and evaporated. The residue is purified, preferably by chromatography on silica gel to obtain the tripeptide of formula Z—L—Pro—L—(N—Me)-Leu—D—Ala—OMe.

Said last-named compound is subjected to amidation. Preferred conditions include treating the latter compound with a substantially saturated solution of ammonia in an inert organic solvent, for example, methanol or ethanol, at 0° to 10° C for 2 to 4 days. The solvent is evaporated and the residue crystallized to obtain the tripeptide of formula Z—L—Pro—L—(N—Me)-Leu—D—Ala—NH$_2$.

The amino protecting group (Z) of the latter compound is removed, preferably by hydrogenation in the presence of a noble metal catalyst in the presence of hydrochloric acid as described immediately above, to obtain the tripeptide derivative H—L—Pro—L—(-N—Me)Leu—D—Ala—NH$_2$, i.e. the compound of formula 1 wherein $R^1$ is $CH_3$, $R^2$ is $CH_2CH(CH_3)_2$, $R^3$ is $NH_2$ and Y is the amino acid residue D—Ala, in the form of the hydrochloric acid addition salt. The acetic acid addition salt of the latter tripeptide derivative of formula 1 is obtained preferably by subjecting said hydrochloric acid addition salt to ion exchange chromatography on a column of carboxymethyl cellulose absorbent (Whatmann CM-23) using ammonium acetate buffer as eluant. If desired the acetic acid addition salt of the latter tripeptide derivative of formula 1 is subjected to repeated lyophilization from water to obtain the latter tripeptide derivative of formula 1 in the form of the free base.

The tripeptide derivative of formula 1 in which $R^1$ is hydrogen, $R^2$ is $CH_2CH(CH_3)_2$, $R^3$ is $NH(CH_2)_4NH_2$ and Y is the amino acid residue Gly is readily prepared by subjecting the compound of formula Z—L—Pro—L—Leu—Gly—OEt to hydrolysis to obtain the corresponding acid of formula Z—L—Pro—L—Leu—Gly—OH. Said last-named acid is transformed to an activated ester and the latter is condensed with mono-(t-butoxycarbonyl)-1,4-diaminobutane to give the intermediate of formula 2 Z—L—Pro—L—Leu—Gly—NH(CH$_2$)$_4$NH—Boc. The amino protecting groups of the latter compound are removed to obtain corresponding tripeptide derivative of formula 1 in which $R^1$ is hydrogen, $R^2$ is $CH_2CH(CH_3)_2$, $R^3$ is NH(CH$_2$)$_4$NH$_2$ and Y is the amino acid residue Gly.

In a preferred embodiment of the preparation of the latter tripeptide derivative of formula 1 the starting material, the tripeptide of formula Z—L—Pro—L—Leu—Gly—OEt, described by W. D. Cash, J. Org. Chem., 26, 2136 (1961) is treated with a hydrolyzing agent to obtain the corresponding acid of formula Z—L—Pro—L—Leu—Gly—OH. For basic hydrolysis a preferred method involves subjecting the tripeptide ester to the action of strong base, for example, sodium or potassium hydroxide, in the presence of sufficient water to effect hydrolysis of the ester. The hydrolysis is performed using a suitable solvent, for example, methanol or ethanol. The reaction mixture is maintained at a temperature of about 10° to 30° C for 15 to 30 min. The reaction mixture is then rendered acidic with an acid, for example, hydrochloric acid, sulfuric acid and the like. The precipitate is collected and crystallized to obtain the corresponding acid of formula Z—L—Pro—L—Leu—Gly—OH.

The above acid is treated with a reagent for transforming an amino or peptide acid to the corresponding activated ester followed by the condensation of the activated ester with a mono protected amino(lower)alkyl amine. This reaction is effected by reacting the corresponding acid with 1.1 to 1.5 molar equivalents of dicyclohexylcarbodiimide and 1.1 to 2.1 molar equivalents of 1-hydroxybenzotriazole followed by the addition of approximately equimolar equivalents of mono-(t-butoxycarbonyl)-1,4-diaminobutane hydrochloride and an organic base, preferably N-ethylmorpholine, in an inert organic solvent, for example, ethyl acetate, dimethylformamide or tetrahydrofuran at a temperature of from about 0° to 30° C, and reaction times of from three to ten hours. The precipitate is removed, the filtrate evaporated and the residue is dissolved in ethyl acetate. The solution is washed, dried, evaporated and the residue purified, preferably by chromatography on silica to obtain the intermediate of formula 2, Z—L—Pro—L—Leu—Gly—NH(CH$_2$)$_4$NH—Boc.

The amino protective groups Z and Boc are removed from said last-named compound to obtain the tripeptide derivative H—L—Pro—L—Leu—Gly—NH(CH$_2$)$_4$NH$_2$, i.e. the compound of formula 1 wherein $R^1$ is H, $R^2$ is $CH_2CH(CH_3)_3$, $R^3$ is NH(CH$_2$)$_4$NH$_2$, and Y is the amino acid residue Gly. The two amino protective groups may be removed simultaneously, for example, by using a strong acid, i.e. hydrobromic acid in acetic acid or hydrofluoric acid, or preferably the amino protective groups may be removed, in a stepwise manner as follows. The above amino protected tripeptide is subjected to hydrogenation as described above in the presence of a noble metal catalyst in an inert solvent, preferably 5% palladium on charcoal in acetic acid, in order to remove the amino protecting group, benzyloxycarbonyl (Z). The mixture is filtered and the filtrate cooled to about 0° to 10° C and treated with a moderately strong acid to remove the remaining amino protecting group, t-butoxycarbonyl (Boc). An example of such an acid is anhydrous hydrogen chloride which is either added directly to the above cooled filtrate or a solution of the acid in an inert organic solvent, for example, ethyl acetate, or tetrahydrofuran is added. The mixture is stirred at about 0° to 30° C for about one to four hours and evaporated to obtain said tripeptide derivative of formula 1 H—L—Pro—L—Leu—Gly—NH(CH$_2$)$_4$NH$_2$ as the hydrochloric acid addition salt. The acetic acid addition salt of the latter tripeptide derivative of formula 1 is obtained by subjecting said hydrochloric acid addition salt to ion exchange chromatography, preferably on an anion exchange resin (Baker CGA-540) in the acetate form. If desired, said acetic acid addition salt of the latter tripeptide derivative of formula 1 is subjected to repeated lyophilization from water to obtain the latter tripeptide derivative of formula 1 in the form of the free base.

Finally, it will be apparent to those skilled in the art that equivalent amino or carboxyl protecting groups, equivalent methods of coupling peptide fragments, and equivalent methods for removal of the protecting groups, other than those disclosed herein may be used in the embodiments of this invention without departing from the scope and spirit of the invention. Such apparent alternations are intended to be included within the scope of this invention.

The following formulae and examples illustrate further this invention.

EXAMPLE 1

Benzyloxycarbonyl—L—prolyl—DL—(N—dimethylamino)leucyl—glycine Ethyl Ester (Z—Pro—N[N(CH$_3$)$_2$]CH[CH$_2$CH(CH$_3$)$_2$]CO—Gly—OEt)

a. Benzyloxycarbonyl-L-proline (12.45 g, 50 mmoles) in dry methylene chloride (50 ml) is added to a solution at 0° C of isovaleraldehyde N,N-dimethylhydrazone (7.05 g, 55 mmoles) and ethyl isocyanoacetate (6.21 g, 55 mmoles) in dry methylene chloride (50 ml). The mixture is stirred at room temperature for 4 days, washed with 5% sodium bicarbonate solution and saturated sodium chloride solution, dried, filtered and the filtrate evaporated. The residue is subjected to chromatography on silical gel using chloroform-methanol (98:2) as eluant. Evaporation of the solvent gives the title compound.

b. In the same manner but replacing benzyloxycarbonyl-L-proline with t-butoxycarbonyl-L-proline and replacing isovaleraldehyde N,N-dimethylhydrozone with methylamino-N-isopentylidene, the two isomers A and B, of t-butoxycarbonyl-L-prolyl-DL-(N-methyl)leucyl-glycine ethyl ester (Boc—L—Pro—N(CH$_3$)CH[CH$_2$CH(CH$_3$)$_2$]CO—Gly—OFt are obtained; isomer A $[\alpha]_D^{25} = +31.8°$(c = 1, dimethylformamide), nmr (CDCl$_3$) δ 1.0 (m, 6H), 1.3 (t, J = 7Hz, 3H), 1.4 (s, 9H), 3.1 (s, 3H), 4.2 (q, J = 7Hz). Isomer B, $[\alpha]_D^{25} = -76.7°$ (c = 1, dimethyl- formamide), mass spectrometry (m/e): 427 (M$^+$).

c. In the same manner but replacing benzyloxycarbonyl-L-proline with t-butoxycarbonyl-L-proline and replacing isovaleraldehyde N,N-dimethylhydrazone with a mixture of formaldehyde and isobutylamine, t-butoxycarbonyl-L-prolyl-(N-isobutyl)-glycyl-glycine glycine ethyl ester (Boc—L—Pro—N[CH$_2$CH(CH$_3$)$_2$]CH$_2$CO—Gly—OE) dimethylformamide), obtained: nmr (CDCl$_3$) δ0.9 (6H), 1.25 (3H), 1.40 (9H), 2.0 (5H), 3—5 (11H), 7.8 (1H).

d. In the same manner but replacing isovaleraldehyde N,N-dimethylhydrazone with a mixture of 1,1-diethylhydrazine and acetaldehyde, benzyloxycarbonyl-L-prolyl-DL-(N-diethylamino)- alanyl-glycine ethyl ester (Z—L—Pro—N[N(C$_2$H$_5$)$_2$]CH(CH$_3$)CO—Gly—OE is obtained.

e. In the same manner but replacing isovaleraldehyde N,N-dimethylhydrazone with a mixture of 1,1-di(n-propyl)hydrazine and isobutyraldehyde, benzyloxycarbonyl-L-prolyl-DL-[N-di- (n-propyl)amino]valyl-glycine ethyl ester (Z—L—Pro—N[N(CH$_2$CH$_2$CH$_3$)$_2$]CH[CH(CH$_3$)$_2$]CO—Gly—OEt is obtained.

f. In the same manner but replacing isovaleraldehyde N,N-dimethylhydrazone with a mixture of ethylamine and isobutyraldehyde, benzyloxycarbonyl—L—prolyl—DL—(N-ethyl)valyl-glycine ethyl ester (Z—L—Pro—N(C$_2$H$_5$)CH[CH(CH$_3$)$_2$]CO—Gly—OEt) is obtained.

EXAMPLE 2

Benzyloxycarbonyl—L—prolyl—DL—(N—dimethylamino) leucyl—glycinamide

Z—Pro—N[N(CH$_3$)$_2$]CH[CH$_2$CH(CH$_3$)$_2$]CO—Gly—NH$_2$ a. The intermediate, benzyloxycarbonyl-L-prolyl-DL-(N-dimethylamino) leucyl-glycine ethyl ester, (8.33 g, 17 mmoles, described in Example 1 (a) is dissolved at 0°C in a saturated solution of anhydrous ammonia in dry methanol (150 ml) and allowed to stand at 0°C for 3 days. The mixture is evaporated under reduced pressure and the residue is subjected to chromatography on silica gel using chloroform-methanol (95:5) as eluant. The two isomers A and B, of the title compound are eluted separately.

Isomer A, nmr (CDCl$_3$) δ0.97 (d, J =6Hz), 2.28 (s, 6H), 5.00 (s, 2H), 7.29 (s, 5H).

Isomer B, nmr (CDCl$_3$) δ0.95(t, J =6Hz, 6H), 2.25 (s, 6H), 5.10 (s, 2H), 7.29 (s, 5H).

b. In the same manner but replacing benzyloxy- carbonyl-L-prolyl-DL-(N-dimethylamino) leucyl-glycine ethyl ester with an equivalent amount of isomer A of -butoxy- carbonyl-L-proly-DL-(N-methyl) leucyl-glycine ethyl ester (described in Example 1 (b), the isomer A of -butoxycarbonyl- L-prolyl-DL-(N-methyl) leucyl-glycinamide (Boc—L—Pro—N(CH$_3$)CH[CH$_2$CH(CH$_{311}$)$_2$]CO—Gly—NH$_2$) is obtained, m.p. 130°–132°C, $[\alpha]25/D =+50.2°$ (c =2, dimethylformamide).

In the same manner but replacing benzyloxycarbonyl- L-prolyl-DL-(N-dimethylamino) leucyl-glycine ethyl ester with an equivalent amount of isomer B of -butoxycarbonyl-L-proly- DL-(N-methyl) leucyl-glycine ethyl ester (described in Example 1(b), then the isomer B of -butoxycarbonyl-L-prolyl- DL-(N-methyl) leuceylglycinamide (Boc—L—Pro—N(CH$_3$)CH[CH$_2$-CH(CH$_3$)$_2$]Gly—NH$_2$ is obtained, mass spectrometry (m/e): 398 (m$^+$).

c. In the same manner but replacing benzyloxycarbonyl- L-prolyl-DL-(N-diemthylamino) leucyl-glycine ethyl ester with an equivalent amount of -butoxycarbonyl-L-prolyl-(N-isobutyl)- glycyl-glycine ethyl ester (described in Example 1 (c)), -butoxycarbonyl-L-prolyl-(N-isobutyl)glycly-glycinamide (Boc—L—Pro—N[CH$_2$CH(CH$_3$)$_2$]CH$_2$CO—Gly—NH$_2$]is obtained: m.p. 92°–95°C, nmr (CDCl$_3$) δ0.9 and 1.03 (doublets, J =2.5 Hz, 6H), 1.4 (s, 9H).

EXAMPLE 3

L-Prolyl-DL-(N-dimethylamino)leucyl-glycinamide hydrochloride

1; R$^1$= N(CH$_3$)$_2$, R$^2$ = CH$_2$CH(CH$_3$)$_2$, R$^3$ = NH$_2$, Y = Gly;

H—L—Pro—N[N(CH$_3$)$_2$]CH[CH$_2$CH(CH$_3$)$_2$]CO—Gly—NH$_2$. HCl a. A mixture of benzyloxycarbonyl-L-prolyl-DL-(N-dimethylamino)leucyl-glycinamide [1.595 g, 3.46 mmoles, isomer A, described in Example 2(a)]and 5% palladium on charcoal catalyst (0.207 g) in methanol is stirred under an atmosphere of hydrogen for 17 hr with the hydrogenation vessel connected to a flask containing a stirred sodium hydroxide solution (4n, 100 ml). The catalyst is removed by filtration. Methanolic hydrochloric acid (0.94N, 3.7 ml, 3.47 mmoles) is added to the filtrate and the latter is evaporated under reduced pressure. The residue is decolorized with active charcoal in anhydrous methanol, filtered and the filtrate evaporated under reduced pressure. The residue is triturated with diethyl ether, ethyl acetate and diethyl ether and dried under reduced pressure over phosphorus pentoxide to give isomer A of the title compound; $[\alpha]_D^{25} =-43.9°$ (c = 2, dimethylformamide), nmr (DMSO-d$_6$) δ 0.9 (d, J = 5Hz, 6 H), 2.57 (s, 6H).

In the same manner but replacing isomer A with an equivalent amount of the corresponding isomer B of benzloxycarbonyl-L-prolyl-DL-(N-dimethylamino)leucyl-glycinamide [described in Example 2(a)], the corresponding isomer B of the title compound is obtained: $[\alpha]_D^{25} = -33°$ (c = 2, dimethylformamide).

b. A solution of anhydrous hydrogen chloride in dry ethyl acetate (1.5N, 55 ml, 82.5 mmoles) is added dropwise over 40 min. to an ice bath cooled suspension of isomer A of t-butoxycarbonyl-L-prolyl-(N-Methyl)-leucyl-glycinamide [6.56 g, 16.5 mmoles, described in Example 2(b)]. The mixture is stirred at ice bath temperature for 30 min. and at room temperature for 17 hr. The solvent is decanted, the solid is triturated with dry ethyl acetate and the solvent decanted. The residue is dissolved in anhydrous methanol, the solution filtered and the filtrate evaporated under reduced pressure. The residue is triturated with ethyl acetate-petroleum ether (1:1), diethyl ether-petroleum ether (1:1) and diethyl ether. The residue is dried under reduced pressure over phosphorus pentoxide and potassium hydroxide to give isomer A of L-prolyl-DL-(N-methyl)leucyl-glycinamide hydrochloride [(1; $R^1$ = $CH_3$, $R^2$ = $CH_2CH(CH_3)_2$, $R^3$ = $NH_2$, Y = Gly; H—L—Pro—N(CH$_3$)CH[CH$_2$CH(CH$_3$)$_2$]CO—Gly—NH$_2$], mass spectrometry (m/e): 298 (M$^+$).

In the same maner but replacing isomer A of t-butoxycarbonyl-L-prolyl-DL-(N-methyl)leucyl-glycinamide with an equivalent amount of isomer B of t-butoxycarbonyl-L-prolyl-DL-(N-methyl)leucylglycinamide (described in Example 2(b)), isomer B of L-prolyl-DL-(N-methyl)leucyl-glycinamide hydrochloride [1; L $R^1$ = $CH_3$, $R^2$ = $CH_2CH(CH_3)_2$, $R^3$ = $NH_2$, Y = Gly; H—L—Pro—N(CH$_3$)CH[CH$_2$CH(CH$_3$)$_2$]CO—Gly—NH$_2$]is obtained; mass spectrometry (m/e): 298 (M$^+$). c. In the same manner as described in Example 3(b) but replacing isomer A of t-butoxycarbonyl-L-prolyl-DL-(N-methyl)leucylglycinamide with an equivalent amount of t-butoxycarbonyl-L-prolyl(N-isobutyl)glycyl-glycinamide, L-prolyl-(N-isobutyl)glycylglycinamide hydrochloride [1; $R^1$ = $CH_2CH(CH_3)_2$, $R^2$ = H, Y = Gly, $R^3$ = $NH_2$; H—L—Pro—N[CH$_2$CH(CH$_3$)$_2$]CH$_2$CO—Gly—NH$_2$] is obtained; mass spectrometry (m/e): 284 (M$^+$).

EXAMPLE 4

L-Prolyl-DL-(N-dimethylamino)leucyl-glycine-4-amino-n-butyl-amide dihydrochloride; 1; $R^1$ = $N(CH_3)_2$, $R^2$ = $CH_2CH(CH_3)_2$, $R^3$ = $NH(CH_2)_4NH_2$, Y = Gly;
(H—L—Pro—N[N(CH$_3$)$_2$]CH[CH$_2$CH(CH$_3$)$_2$]CO—Gly—NH(CH$_2$)$_4$NH$_2$ . 2 HCl a. A solution of benzyloxycarbonyl-L-prolyl-DL-(N-dimethylamino)leucyl-glycine ethyl ester (4.45 g, 9.07 mmoles, described in Example 1(a)) and 1N sodium hydroxide (12.25 ml) in methanol (23 ml) is stirred at room temperature for 20 hr. Saturated sodium chloride solution (50 ml) is added and the precipitate removed by filtration. The filtrate is cooled to 0° C and acidified with 1N hydrochloric acid (13.3 ml). The mixture is extracted with chloroform. The organic extract is washed with water to neutral, dried over magnesium sulfate and evaporated under reduced pressure to give benzyloxycarbonyl-L-prolyl-DL-(N-dimethylamino)-leucyl-glycine; nmr (CDCl$_3$) δ 0.93 (6H), 2.53 (6H), 8.6 (1H).

b. N,N'-Carbonyldiimidazole (1.19 g, 7.5 mmoles) is added to a stirred solution at −15° C of benzyloxycarbonyl-L-prolyl-DL-(N-dimethylamino)leucyl-glycine [3.477 g, 7.5 mmoles, described in Example 4(a)]in dry dimethylformamide (14 ml) maintaining a dry atmosphere. The mixture is stirred at −15° C for 30 min. A solution of mono-(t-butoxycarbonyl)-1,4-diaminobutane hydrochloride [1.685 g, 7.5 mmoles, prepared as described by R. Geiger, Annalen, 750, 165 (1971)]and triethylamine (1.25 ml) in dry dimethylformamide (6 ml) is added. The mixture is stirred at room temperature for 20 hr. and evaporated. The residue is taken up in ethyl acetate (200 ml) and washed with 10% sodium bicarbonate solution, 20% sodium chloride solution, 10% citric acid solution, and 20% sodium chloride solution. The organic phase is dried over magnesium sulfate and evaporated. The residue is subjected to chromatography on silica gel using chloroform-methanol-pyridine(95:5:1) to elute separately the two isomers, A and B, of benzyloxycarbonyl-L-prolyl-DL-(N-dimethylamino)leucyl-glycine-4-t-butoxycarbonyl-amino-n-butyl amide:

Isomer A; nmr (CDCl$_3$) δ 0.99 (d, J = 6Hz, 6H), 1.42 (s, 9H), 2.65 (6H), 5 (s, 2H), 7.25 (5H).

Isomer B, nmr (CDCl$_3$) δ 0.95 (t, J = 6Hz, 6H), 1.43 (s, 9H), 5.10 (s, 2H), 7.30 (s, 5H).

c. A mixture of isomer A of benzyloxycarbonyl-L-prolyl-DL-(N-dimethylamino)leucyl glycine-4-t-butoxycarbonylamino-n-butyl-amide [2.26 g, 3.58 mmole, described in Example 4(b)]and 5% palladium on charcoal catalyst (0.250 g) in acetic acid (50 ml) is stirred under an atmosphere of hydrogen for 21 hr with the hydrogenation vessel connected to a flask containing a stirred solution of sodium hydroxide (4N, 100 ml). The catalyst is removed by filtration, the filtrate cooled in ice-water and a solution of hydrogen chloride in dry ethyl acetate (1.6 N, 12 ml) is added dropwise. The mixture is stirred at room temperature for two hours with exclusion of moisture. The solvent is evaporated under reduced pressure and traces of acetic acid are removed by azeotropic evaporation with dry benzene. The residue is subjected to chromatography on a column of a cross-linked dextran absorbent (Sephadex LH-20) using methanol. The eluant is decolorized with active charcoal, filtered and evaporated. The residue is triturated with anhydrous diethyl ether and dried under reduced pressure over phosphorus pentoxide to give isomer A of the title compound: $[\alpha]_D^{25}$ = −43.6° (c = 2, dimethylformamide);

Analysis for $C_{19}H_{38}N_6O_3$ 2 HCl: Calc'd: C, 47.70; H, 8.52; N, 17.60; Cl, 14.86; Found: C, 47.10; H, 8.55; N, 17.55; Cl, 15.24.

In the same maner manner replacing isomer A of benzyloxycarbonyl-L-prolyl-DL-(N-dimethylamino)-leucyl-glycine-4-t-butoxycarbonylamino-n-butyl-amide with the corresponding isomer B [described in Example 4(b)], the corresponding isomer B of the title compound is obtained: $[\alpha]_D^{25}$ −18.6° (c = 2, dimethylformamide):

·Analysis for $C_{19}H_{36}N_6O_3$ 2 HCl H$_2$O: Calc'd: C, 46.62; H, 8.64; N, 17.20; Found: C, 46.88; H, 8.50; N, 17.51.

d. In the same manner but replacing benzyloxycarbonyl-L-prolyl-DL-(N-diemethylamino)leucyl-glycine ethyl ester with an equivalent amount of benzyloxycarbonyl-L-prolyl-DL-(N-diethylamino)-alanyl-glycine ethyl ester [described in Example 1(d)] and replacing mono-(t-butoxycarbonyl)-1,4-diaminobutane hydrochloride with an equivalent amount of diethylamine, L-prolyl-DL-(N-diethylamino)-alanyl-glycine diethylamide hdyrochloride [1; $R^1$ = $N(CH_2CH_3)_2$, $R^2$ = $CH_3$, $R^3$ = $N(CH_2CH_3)_2$, Y = Gly] is obtained.

e. In the same manner but replacing benzyloxycarbonyl-L-prolyl-DL-(N-dimethylamino)leucyl-glycine ethyl ester with an equivalent amount of benzyloxycarbonyl-L-prolyl-DL-[N-di(n-propyl)amino]valyl-glycine ethyl ester [described in Example 1(e)] and replacing mono-(t-butoxycarbonyl)-1,4-diaminobutane hydrochloride with an equivalent amount of n-propylamine, L-prolyl-DL-[N-di(n-propyl)amino]valyl-glycine n-propylamide hydrochloride [1; $R^1$ =

N(CH$_2$CH$_2$CH$_3$)$_2$, R$^2$ = CH(CH$_3$)$_2$, R$^3$ = NH(CH$_2$CH$_2$CH$_3$), Y = Gly; H—L—Pro—N[N(CH$_2$CH$_2$CH$_3$)$_2$]CO-Gly-NH(CH$_2$CH$_2$CH$_3$)] is obtained.

f. In the same manner but replacing benzyloxycarbonyl-L-prolyl-DL-(N-dimethylamino)leucyl-glycine ethyl ester with an equivalent amount of benzyloxycarbonyl-L-prolyl-DL-(N-ethyl)valylglycine ethyl ester [described in Example 1(f)] and replacing mono(t-butoxycarbonyl)-1,4-diaminobutane hydrochloride with an equivalent amount of methylamine, L-prolyl-DL-(N-ethyl)valylglycine methylamide hydrochloride [1; R$^1$ = CH$_2$CH$_3$, R$^2$ = CH(CH$_3$)$_2$, R$^3$ = NHCH$_3$, Y = Gly; H—L—Pro—N(CH$_2$CH$_3$)CH[CH(CH$_3$)$_2$]CO—Gly—NHCH$_3$] is obtained.

EXAMPLE 5

Alternative synthesis of t-butoxycarbonyl-L-prolyl-L-(N-methyl)leucylglycine ethyl ester (Boc—L—Pro—N(CH$_3$)CH[CH$_2$CH(CH$_3$)$_2$]CO—Gly—OEt (isomer B, previously described in Example 1(b))

A solution of Z-L-(N-Me)Leu-OH [4.2 g, 15 mmoles, prepared as described by J. R. Coggins and N. Leo Benoiton, Can. J. Chem., 49, 1968 (1972)], 2,4,5-trichlorophenol (2.96 g, 15 mmoles) and dicyclohexylcarbodiimide (3.09 g, 15 mmoles) in dry methylene chloride (21 ml) is stirred at −15° C for one hr and then at room temperature for 2 hr. The pecipitate is removed by filtration and the filtrate is evaporated to give Z—L—(N—Me)-Leu—OTcp.

A solution of Z—L—(N—Me)Leu—OTcp (15 mmoles, described above) in dimethylformamide (10.5 ml) is added to a solution of 0° C of glycine ethyl ester hydrochloride (2.09 g, 15 mmoles) and N-ethylmorpholine (1.92 ml, 15 mmoles) in dimethylformamide (35 ml) and the mixture is stirred at 0° C for 30 min and then at room temperature for 20 hr. The solvent is removed by evaporation and the residue is subjected to chromatography on silica gel using chloroform-ethyl acetate (85:15) as eluant. Evaporation of the eluates gives Z—L—(N—Me)Leu—Gly—OEt, nmr (CDCl$_3$) δ 0.93 (6H), 1.27 (3H), 2.85 (3H), 3.97 (2H), 4.20 (2H), 5.17 (2H), 7.34 (5H).

A solution of hydrobromic acid in acetic acid (30–32%, 4.9 ml, 24 mmoles) is added to a solution of Z—L—(N—Me)Leu—Gly—OEt (2.9 g, 7.96 mmoles, described above) in acetic acid (4.7 ml) and the resulting mixture is stirred at room temperature for 4.5 hr. The solvent is removed by evaporation under reduced pressure and the esidue residue subjected to repeated azeotropic distillation with benzene-methanol. The resulting residue is dried under reduced pressure over potassium hydroxide to give [H—L—(N—Me)Leu—Gly—OEt]HBr.

A solution of Boc- L—Pro—OH (0.645 g, 3 mmoles), 1-hydroxybenzotriazole (0.810 g, 6 mmoles) and dicyclohexylcarbodiimide (0.680, 3.3 mmoles) in dry tetrahydrofuran (15 ml) is stirred at −5° C for one hr and then at 25° C for one hr. The mixture is cooled to 0° C and treated with a solution at 0° C of [H—L—(-N—Me)Leu—Gly—OEt]Hbr (3 mmoles, described above) and N-ethylmorpholine (0.384 ml, 3 mmoles) in dry tetrahydrofuran (14 ml). The mixture is stirred at 0° C for 30 min and then at room temperature for 40 hr. The pecipitate is removed by filtration and the filtrate is evaporated under reduced pressure. The residue is dissolved in ethyl acetate (100 ml). The solution is washed with ice-cold 1N citric acid, water, 5% sodium bicarbonate solution and saturated sodium chloride solution. The organic phase is dried over magnesium sulfate and evaporated. The residue is subjected to chromatography on silica gel using chloroform-ethyl acetate-pyridine (50:50:01) as eluant to give the title compound, t-butoxycarbonyl-L-propyl-L-(N-methyl)-leucylglycine ethyl ester; [α]$_D^{25}$ = −73.1° (c = 1, dimethylformamide). The title compound obtained by the above method is identical to isomer B of t-butoxycarbonyl-L-prolyl-DL-(N-methyl)leucyl-glycine ethyl ester as obtained by the method described in Example 1(b).

EXAMPLE 6

L-prolyl-L-(N-methyl)leucyl-D-alaninamide (H-Pro-L-(N-Me)Leu-D-Ala-NH$_2$) [1; R$^1$ = CH$_3$, R$^2$ = CH$_2$CH(CH$_3$)$_2$, R$^3$ = NH$_2$, Y = D-Ala]

Benxyloxycarbonyl-L-(N-methyl)leucine (14.9 g, 50 mmoles), D-alanine methyl ester (7.0 g, 50 mmoles) and 1hydroxybenzotriazole (13.5 g, 10 mmoles) are dissolved in a mixture of dry tetrahydrofuran (300 ml) and dimethylformamide (70 ml). The solution is cooled to 0° C and N-ethylmorpholine (6.42 ml; 50 mmoles) is added followed by dropwise addition of a solution of dicyclohexylcarbodiimide (10.3 g; 50 mmoles) in dry tetrahydrofuran (80 ml). The reaction mixture is stirred at 0° C for 1 hour, at room temperature for a further hour, filtered and the solvents removed uner reduced pressure. The residue is taken in ethyl acetate and extracted with water and saturated sodium chloride solution. The residue left after drying and evaporation of the ethyl acetate layers is subjected to chromatography on silica gel (1 kg; CHCl$_3$ containing 2% MeOH). Evaporation of the eluants gives Z—L—(-N—Me)Leu—D—Ala—OMe; nmr (CDCl$_3$) δ 2.86 (3H, s), 3.74 (3H, s), 5.25 (; 2H, s), 7.42 (5H, s).

A mixture of benzyloxycarbonyl-L-(N-methyl)leucyl-D-alanine methyl ester (10.5 g, 28.8 g, described above) and 5% palladium on charcoal (1.0 g) in acetic acid (120 ml) and hydrochloric acid (2N, 14.4 ml, 28.8 mmoles) is stirred under an atmosphere of hydrogen for 24 hr. The catalyst is removed by filtration and the filtrate evaporated to give a residue of H—L—(-N—Me)Leu—D—Ala—OMe . HCl. A solution of the latter compound (28.8 mmoles), 1-hydroxybenzotriazole (3.9 g, 28.8 mmoles), benzyloxycarbonyl-L-proline p-nitrophenyl ester (10.7 g, 28.8 mmoles) and N-ethylmorpholine (3.7 ml, 28.8 mmoles) in dimethylformamide (70 ml) is stirred at 0° C for three days. After evaporation of the solvents under reduced pressure the residue is dissolved in ethyl acetate and washed with water, saturated sodium bicarbonate solution, water and saturated sodium chloride solution. The organic phase is dried over magnesium sulfate and evaporated. The residue is subjected to chromatography on silica gel using chloroform-methanol (98:2). The eluants are evaporated to give benzyloxycarbonyl-L-prolyl-L-(N-methyl)leucyl-D-alanine methyl ester (Z—L—Pro—L—(N—Me)Leu—D—Ala—OMe); nmr (CDCl$_3$): δ 0.95 (d, 6H), 2.87 and 3.0 (two s, 3H), 3.72 (s, 3H), 7.4 (s, 5H).

The latter compound (1.7 g, 3.68 mmoles) is dissolved at 0° C in methanol saturated with ammonia (85 ml) and allowed to stand at 0° for 3 days. The solvent is removed by evaporation and the residue is crystallized from isopropyl ether-acetone to give benzyloxycarbonyl-L-prolyl-L-(N-methyl)leucyl-D-alaninamide (Z-L-pro-L-(N-Me)Leu-D-Ala-NH$_2$); m.p. 148°–150° C, Analysis for C$_{23}$H$_{34}$N$_4$O$_5$: Calc'd: C, 61.86; H, 7.67; N, 12.55%; Found: C, 61.67; H, 7.82, N, 12.66%.

A mixture of Z—L—Pro—L—(N—Me)-Leu—D—Ala—NH$_2$ (1.29 g, 2.9 mmoles, described above) and 5% palladium on charcoal (0.13 g) in acetic acid (20 ml) and hydrochloric acid (1N, 2.9 ml) is stirred under and atmosphere of hydrogen for 20 hr. The catalyst is removed by filtration and the filtrate is lyophilized to give the title compound as the hydrochloric acid addition salt. The residue is subjected to ion exchange chromatography on a column of carboxymethyl cellulose (Whatmann CM-23) using 0.04N aqueous ammonium acetate. The eluant is lyophilized to give the title compound as the acetic acid addition salt, $[\alpha]_D^{25} = -77.6°$ ($c = 1$, 1% acetic acid).

Repeated lyophilization of the latter compound from water gives the title compound as the free base, nmr (CDCl$_3$) $\delta$ 0.90 (s, 6H), 1.22 (d, J = 7Hz, 3H), 1.45–2.16 (m, H), 2.82 and 2.90 (singlets, 3H), 3.9–5.2 (m, 3H).

In the same manner, by using benzyloxycarbonyl-D-(N-methyl)leucine as the starting material instead of the L-enantiomer described above, L-prolyl-D-(N-methyl)leucyl-D-alaninamide (H—Pro—D—(N—Me)Leu—D—Ala—NH$_2$) is obtained, amino acid analysis: Pro 0.88, Ala 1.00.

EXAMPLE 7

L-prolyl-L-leucyl-glycine-4-amino-n-butyl-amide [1; R$^1$ = H, R$^2$ = CH$_2$CH(CH$_3$)$_2$, R$^3$ = NH(CH$_2$)$_4$NH$_2$, Y = Gly] (H—L—Pro—L-Leu—Gly—NH(CH$_2$)$_4$NH$_2$)

1N sodium hydroxide (3.02 ml) is added dropwise to a stirred suspension at 0° C of benzyloxycarbonyl-L-prolyl-L-leucyl-glycine ethyl ester [1.0 g, 2.24 mmoles, prepared as described by W. O. Cash, J. Org. Chem., 26, 2136 (1961)] in methanol (5.6 ml) and the solution is stirred at 25° C for 20 min. The solution is diluted with saturated sodium chloride (23 ml), cooled to 0° C and acidified with 1N hydrochloric acid (3.3 ml). The mixture is stirred at 0° C for 20 min. The solid is collected, washed with cold water, dried uner reduced pressure over phosphorus pentoxide, and crystallized from methanol-water to give Z—L—Pro—L—Lue—Gly—OH; m.p. 162°–165° C, $[\alpha]_D^{25} = -55.8°$ ($c = 2$, dimethylformamide).

A mixture of the latter compound (9.48 g, 22.6 mmoles) mono-(t-butoxycarbonyl)-1,4-diaminobutane hydrochloride (5.06 g, 22.6 mmoles), N-ethylmorpholine (28.9 ml), 1-hydroxybenzotriazle (6.1 g, 45 mmoles) and dicyclohexylcarbodiimide (4.98 g, 24.85 mmoles) in dimethylformamide (225 ml) is stirred at 0° C for one hour and then at 25° C for 4 hr. The pecipitate is removed by filtration and the solvent evaporated. The residue is dissolved in ethyl acetate, the precipitate is removed, and the filtrate is washed with 10% sodium bicarbonate solution, water, 10% citric acid solution and water. The organic phase is dried over magnesium sulfate and the solvent evaporated. The residue is subjected to chromatography on silica gel using chloroform-methanol-pyridine (98:2:1) as the eluant followed by evaporation of the eluant to give Z—L—Pro—L—Leu—Gly—NH(CH$_2$)$_4$NH—Box, nmr (CDCl$_3$): $\delta$0.92 (6H), 1.42 (9H), 5.16 (2H), 7.36 (5H).

A mixture of the latter compound (7.4 g, 12.55 mmoles) and 5% palladium on charcoal (0.505 g) in acetic acid (50 ml) is stirred under an atmosphere of hydrogen for 5 hr with the hydrogenation vessel connected to a flask containing a stirred solution of sodium hydroxide 4N, 250 ml). The mixture is filtered and the filtrate cooled in an ice bath. A solution of hydrogen chloride in dry ethyl acetate (4.6N, 16 ml) is added dropwise and the mixture is stirred at 10° C for 30 min and then at room temperature for 3 hr. The solvent is evaporated and the residue is dissolved in benzene and the solvent is again evaporated. The residue is dissolved in methanol, active charcoal is added, filtered and the solvent evaporated from the filtrate to give the title compound as the hydrochloric acid addition salt. The latter compound is dissolved in 0.1 N hydrochloric acid and subjected to ion exchange chromatography on an anion exchange resin (Baker CGA-540) in the acetate form. The eluants are evaporated, the residue triturated with diethyl ether and petroleum ether and dried to give the title compound as the acetic acid addition salt;

Anal. for C$_{17}$H$_{33}$N$_5$O$_3$.2CH$_3$CO$_2$H. 1/2 H$_2$O (484.6): Calc'd: C, 52.04; H, 8.73; N, 14.45; CH$_3$CO$_2$H, 24.78%; Found: C, 52.13; H, 8.70; N, 14.35; CH$_3$CO$_2$H, 23.2%.

PROCESS

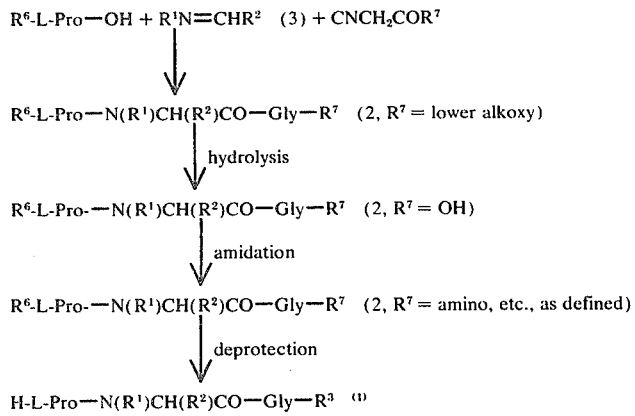

OR

PROCESS

-continued

Z-L-(N—Me)Leu—OH + H—Y—O (lower alkyl) ⟶ Z-L-(N—Me)Leu—Y—O (lower alkyl)

$\xrightarrow{\text{1) deprotection}}$ Z-L-Pro-L-(N—Me)Leu—Y—O (lower alkyl) $\xrightarrow[\text{(2) deprotection}]{\text{(1) amidation}}$ 2)Z-L-Pro-ONP H-L-Pro-L-(N—Me)Leu—Y—NH₂  (1, Y = Gly or D-Ala)

We claim:

1. A compound of formula 1

```
       H-L-Pro—N—CH—C—Y—R³          I
              |   |   ||
              R¹  R²  O
``` in which R¹ is hydrogen, lower alkyl or NR⁴R⁵ wherein R⁴ and R⁵ each are lower alkyl; R² is hydrogen or lower alkyl; R³ is amino, lower alkylamino, di(lower)alkylamino or amino(lower)alkylamino, and Y is one of the amino acid residues Gly or D—Ala with the proviso that when R¹ is NR⁴ R⁵ is lower alkylamino, di(lower)alkylamino or amino(lower)alkylamino and with the further proviso that when R¹ is hydrogen, R² is CH₂CH(CH₃)₂, R³ is amino then Y is D—Ala.

2. A pharmaceutically acceptable acid addition salt of the compound of formula 1 as claimed in claim 1.

3. The corresponding amino protected derivative of the compound of formula 1 as claimed in claim 1 wherein the protecting group is selected from the group consisting of benzyloxycarbonyl, t-butoxycarbonyl, α,α-dimethyl-3,4,-dimethoxybenzyloxycarbonyl, triphenylmethyl and benzyl.

4. L-Prolyl-D-(N-methyl)leucyl-glycinamide, as claimed in claim 1.

5. L-Prolyl-L-(N-methyl)leucyl-glycinamide, as claimed in claim 1.

6. L-Prolyl-(N-isobutyl)glycyl-glycinamide as claimed in claim 1.

7. L-Prolyl-DL-(N-dimethylamino)leucyl n-butyl-amide, as claimed in Claim 1 having a rotation of $_D^{25}$ = -43.6° (c = 2,dimethylformamide).

8. L-Prolyl-DL-(N-dimethylamino)leucyl-glycine-4-amino- n-butyl-amide, as claimed in claim 1 having a rotation of $_D^{25}$ = 18.6° c = 2,dimethylformamide).

9. L-Prolyl-L-(N-methyl)leucyl-D-alaninamide as claimed in claim 1.

10. L-Prolyl-D-(N-methyl)leucyl-D-alaninamide, as claimed in claim 1.

11. L-Prolyl-L-leucyl-glycine-4-amino-n-butyl-amide as claimed in claim 1.

12. A process for preparing a compound of formula 1

```
       H-L-Pro—N—CH—C—Y—R³          (1)
              |   |   ||
              R¹  R²  O
``` in which R¹ is lower alkyl or NR⁴R⁵ wherein R⁴ and R⁵ each are lower alkyl; R² is hydrogen or lower alkyl; R³ is amino, lower alkylamino, di(lower)alkylamino or amino(lower)alkylamino and Y is the amino acid residue Gly with the proviso that when R¹ is NR⁴R⁵, R³ is lower alkylamino di(lower)alkylamino or amino(lower)alkylamino which comprises:

condensation of an enamine or hydrazone of formula 3, R¹N=CHR² (3), in which R¹ and R² are as defined herein with an amino acid of formula R⁶—L—Pro—OH in which R⁶ is an amino protecting group selected from the group consisting of benzyloxycarbonyl, t-butoxycarbonyl, α,α-dimethyl-3,4-dimethoxy benzyloxycarboxyl, triphenylmethyl and benzyl in the presence of an isonitrile of the formula CNCH₂COR⁷ in which R⁷ is lower alkoxy, to obtain the corresponding intermediate of formula 2

R⁶ — L — -Pro— N(R¹)CH(R²)CO — Gly — R⁷     (2)

in which R¹,R²,R⁶ and R⁷ are as defined herein, followed by subjecting the last-named compound to amidation to give the corresponding amide or substituted amide and removal of the protective group(s) to obtain the corresponding peptide derivative of formula 1 in which R¹, R², R³ and Y are as defined herein.

13. A process as claimed in claim 12 in which the transformation of the intermediate of formula 2

R⁶ — L— Pro — N(R¹)CH(R²)CO — Gly — R⁷     (2)

in which R¹,R², R⁶ and R⁷ are as defined therein is carried out by treating said intermediate with ammonia to obtain the corresponding amide, followed by removal of the protective group R⁶ selected from the group consisting of benzyloxycarbonyl, t-butoxycarbonyl, α,α-dimethyl-3,4-dimethoxy benzyloxycarbonyl, triphenylmethyl and benzyl to obtain the corresponding peptide derivative of formula 1 in which R¹ and R² are as defined therein, R³ is amino and Y is the amino acid residue Gly.

14. A process as claimed in claim 13 in which the transformation of the intermediate of formula 2

R⁶ — L — Pro — N(R¹)CH(R²)CO— Gly — R⁷     (2)

in which R¹, R², R⁶ and R⁷ are as defined therein is carried out by treating said intermediate with a hydrolyzing agent to obtain the corresponding acid, treating said acid with an activating agent to give the corresponding activated ester selected from the group consisting of 2,4,5trichlorophenyl, pentachlorophenyl, p-nitrophenyl, and 1-benzotriazolyl, and N,N¹-carbonyldiimidazolide and o-acylura of dicyclohexylcarboxdiimide condensing said activated compound with a lower alkylamine, di(lower)alkylamine or mono protected amino(lower)alkylamine in which the protecting group is selected from the group consisting of benzyloxycarbonyl, t-butoxycarbonyl,α,α-dimethyl 3,4-dimethoxybenzyloxycarbonyol, triphenylmethyl and benzyl to obtain the corresponding substituted amide and removing the protective group(s) from said last-named compound to obtain the corresponding peptide derivative of formula 1 in which R¹ and R² are as defined herein, R³ is lower alkylamino, di(lower)alkylamino or amino(lower)alkylamino and Y is the amino acid residue Gly.

15. A process for preparing a compound of formula 1

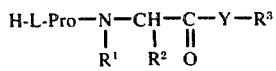 (1)

in which $R^1$ is $CH_3$, $R^2$ is $CH_2CH(CH_3)_2$, $R^3$ is $NH_2$ and Y is the amino acid residue D—Ala which comprises: reacting an activated ester selected from the group consisting of 2,4,5,trichlorophenyl, pentachlorphenyl, p-nitrophenyl and 1-benzotriazolyl of benzyloxycarbonyl-L-(N-methyl)leucine with D-alanine methyl ester to obtain the dipeptide of formula Z—L—(N—Me)Leu—D—Ala—(N—Me)-Leu—treating said last-named compound with hydrogen and a noble metal catalyst and isolating the dipeptide of formula H—L—(N—Me)-Leu—D—Ala—OMe, reacting said last-named compound with an activated ester as defined herein of benzyloxycarbonyl- L-proline and isolating the tripeptide of formula Z—L—Pro—L—(N—Me) Leu—D—Ala—OMe; treating said last-named compound with ammonia and isolating the tripeptide of formula Z—L—Pro—L—(N—Me)-Leu—D—Ala—NH₂; treating said last-named compound with hydrogen and a noble metal catalyst and isolating the corresponding tripeptide derivative of formula 1 in which $R^1$ is $CH_3$, $R^2$ is $CH_2CH(CH_3)_2$, $R^3$ is $NH_2$ and Y is the amino residue D—Ala.

16. A pharmaceutical composition comprising an acid addition salt of a compound of formula 1 as claimed in claim 2 and a pharmaceutically acceptable carrier.

17. A pharmaceutical composition comprising an amino protected derivative of a copound of formula 1 as claimed in claim 3 wherein the protecting group is selected from the group consisting of benzyloxycarbonyl t-butoxycarbonyl, α,α-dimethyl-3,4-dimethoxybenzyloxycarbonyl triphenylmethyl and benzyl and a pharmaceutically acceptable carrier.

18. A method of treating Parkinsonism in warm-blooded animals comprising the oral administration thereto of 0.25–100 mg/kg of an acid addition salt of a compound of formula 1 as claimed in claim 1 or a pharmaceutically acceptable acid addition salt thereof.

19. A method of treating mental depression in warm-blooded animals comprising the oral administration thereto of 0.25–100 mg/kg of a compound of formula 1 as claimed in claim 1 or a pharmaceutically acceptable acid addition salt thereof.

20. A method of treating Parkinsonism in warm-blooded animals comprising the parenteral administration thereto of 0.05–20 mg/kg of an acid addition salt of a compound of formula 1 as claimed in claim 1 or a pharmaceutically acceptable acid addition salt thereof.

21. A method of treating mental depression in warm-blooded animals comprising the parental administration thereto of 0.05–20 mg/kg of an acid addition salt of a compound of formula 1 as claimed in claim 1 or a pharmaceutically acceptable acid addition salt thereof.

* * * * *